US010105211B2

(12) United States Patent
Euteneuer et al.

(10) Patent No.: US 10,105,211 B2
(45) Date of Patent: Oct. 23, 2018

(54) APPARATUS AND METHOD FOR FORMING PILOT HOLES IN BONE AND DELIVERING FASTENERS THEREIN FOR RETAINING AN IMPLANT

(71) Applicant: Rotation Medical, Inc., Plymouth, MN (US)

(72) Inventors: Charles L. Euteneuer, St. Michael, MN (US); Thomas A. Westling, Orono, MN (US); Nathaniel Z. Zenz-Olson, Blaine, MN (US); Michael Witzmann, Minneapolis, MN (US)

(73) Assignee: ROTATION MEDICAL, INC., Plymouth, MN (US)

( * ) Notice: Subject to any disclaimer, the term of this patent is extended or adjusted under 35 U.S.C. 154(b) by 541 days.

(21) Appl. No.: 14/812,374

(22) Filed: Jul. 29, 2015

(65) Prior Publication Data

US 2015/0327858 A1 Nov. 19, 2015

Related U.S. Application Data

(63) Continuation of application No. 13/889,722, filed on May 8, 2013, now Pat. No. 9,125,650, which is a
(Continued)

(51) Int. Cl.
*A61B 17/068* (2006.01)
*A61F 2/08* (2006.01)
(Continued)

(52) U.S. Cl.
CPC .......... *A61F 2/0811* (2013.01); *A61B 17/068* (2013.01); *A61B 17/0642* (2013.01);
(Continued)

(58) Field of Classification Search
CPC .................................................. A61B 17/0682
See application file for complete search history.

(56) References Cited

U.S. PATENT DOCUMENTS

| 511,238 A | 12/1893 | Hieatzman et al. |
| 765,793 A | 7/1904 | Ruckel |
(Continued)

FOREIGN PATENT DOCUMENTS

| CA | 2390508 A1 | 5/2001 |
| EP | 0142225 A1 | 5/1985 |
(Continued)

OTHER PUBLICATIONS

Bahler et al., "Trabecular Bypass Stents Decrease Intraocular Pressure in Cultured Himan Anterior Segments", American Journal Opthalmology, vol. 138, No. 6, pp. 988-994, Dec. 2004.
(Continued)

*Primary Examiner* — Nicholas Woodall
(74) *Attorney, Agent, or Firm* — Seager, Tufte & Wickhem LLP.

(57) ABSTRACT

Apparatus and methods for forming pilot holes in bone and deploying a staple therein for fixing a sheet-like implant to the bone. A pilot hole forming trocar assembly including a trocar and a position retention sleeve can be included. The trocar can be releasably coupled to the position retention sleeve and slide in keyed arrangement within the sleeve when uncoupled. The trocar can include a distal portion having a retractable blade and a pair of pilot hole forming spikes extending distally from the trocar shaft. Once the pilot holes are formed, the position retention sleeve maintains the position relative to the pilot holes while the trocar is removed and a staple delivery device can be inserted in the lumen of the position retention sleeve to deploy a staple in the pilot holes.

20 Claims, 11 Drawing Sheets

Related U.S. Application Data continuation of application No. 13/717,474, filed on Dec. 17, 2012, now Pat. No. 9,247,978.

(60) Provisional application No. 61/577,621, filed on Dec. 19, 2011.

(51) Int. Cl.
    *A61B 17/56* (2006.01)
    *A61B 17/88* (2006.01)
    *A61B 17/064* (2006.01)
    *A61B 17/16* (2006.01)
    *A61B 17/34* (2006.01)

(52) U.S. Cl.
    CPC ...... *A61B 17/0682* (2013.01); *A61B 17/3472* (2013.01); *A61B 17/56* (2013.01); *A61B 17/88* (2013.01); *A61B 17/8872* (2013.01); *A61B 17/1604* (2013.01); *A61B 17/3468* (2013.01); *A61B 2017/3454* (2013.01); *A61B 2017/3488* (2013.01); *A61B 2017/564* (2013.01)

(56) References Cited

U.S. PATENT DOCUMENTS

| | | |
|---|---|---|
| 1,728,316 A | 9/1929 | von Wachenfeldt et al. |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,462,395 A | 7/1984 | Johnson |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gattuma |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gattuma et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | Kckinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,197,933 A | 3/1993 | Waters |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,279,570 A | 1/1994 | Dombrowski et al. |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |

(56) References Cited

U.S. PATENT DOCUMENTS

| | | |
|---|---|---|
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,421,193 A | 6/1995 | Carlin et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hathurst |
| 5,649,963 A | 7/1997 | McDevitt |
| 5,662,683 A | 9/1997 | Kay |
| 5,667,513 A | 9/1997 | Torrie et al. |
| 5,669,882 A | 9/1997 | Pyles |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,973 A | 9/1999 | DiPoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A * | 12/1999 | Person ............ A61B 17/064 606/139 |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,270,503 B1 | 8/2001 | Schieding |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Scmhieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins et al. |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |

(56) References Cited

U.S. PATENT DOCUMENTS

| | | | |
|---|---|---|---|
| 7,144,413 B2 | 12/2006 | Wilford et al. | |
| 7,144,414 B2 | 12/2006 | Harvie et al. | |
| 7,150,750 B2 | 12/2006 | Damarati | |
| 7,153,314 B2 | 12/2006 | Laufer et al. | |
| 7,160,236 B2 | 1/2007 | Ball | |
| 7,160,314 B2 | 1/2007 | Sgro et al. | |
| 7,163,551 B2 | 1/2007 | Anthony et al. | |
| 7,163,563 B2 | 1/2007 | Schwartz et al. | |
| 7,169,157 B2 | 1/2007 | Kayan | |
| 7,189,251 B2 | 3/2007 | Kay | |
| 7,201,754 B2 | 4/2007 | Stewart et al. | |
| 7,214,232 B2 | 5/2007 | Bowman et al. | |
| 7,226,469 B2 | 6/2007 | Benavitz et al. | |
| 7,229,452 B2 | 6/2007 | Kayan | |
| 7,247,164 B1 | 7/2007 | Ritchart et al. | |
| 7,303,577 B1 | 12/2007 | Dean | |
| 7,309,337 B2 | 12/2007 | Colleran et al. | |
| 7,320,692 B1 | 1/2008 | Bender et al. | |
| 7,320,701 B2 | 1/2008 | Haut et al. | |
| 7,322,935 B2 | 1/2008 | Palmer et al. | |
| 7,326,231 B2 | 2/2008 | Phillips et al. | |
| 7,343,920 B2 | 3/2008 | Toby et al. | |
| 7,368,124 B2 | 5/2008 | Chun et al. | |
| 7,377,934 B2 | 5/2008 | Lin et al. | |
| 7,381,213 B2 | 6/2008 | Lizardi | |
| 7,390,329 B2 | 6/2008 | Westra et al. | |
| 7,399,304 B2 | 7/2008 | Gambale et al. | |
| 7,404,824 B1 | 7/2008 | Webler et al. | |
| 7,416,554 B2 | 8/2008 | Lam et al. | |
| 7,452,368 B2 | 11/2008 | Liberatore et al. | |
| 7,460,913 B2 | 12/2008 | Kuzma et al. | |
| 7,463,933 B2 | 12/2008 | Wahlstrom et al. | |
| 7,465,308 B2 | 12/2008 | Sikora et al. | |
| 7,481,832 B1 | 1/2009 | Meridew et al. | |
| 7,485,124 B2 | 2/2009 | Kuhns et al. | |
| 7,497,854 B2 | 3/2009 | Gill et al. | |
| 7,500,972 B2 | 3/2009 | Voegele et al. | |
| 7,500,980 B2 | 3/2009 | Gill et al. | |
| 7,500,983 B1 | 3/2009 | Kaiser et al. | |
| 7,503,474 B2 | 3/2009 | Hillstead et al. | |
| 7,506,791 B2 | 3/2009 | Omaits et al. | |
| 7,559,941 B2 | 7/2009 | Zannis et al. | |
| 7,572,276 B2 | 8/2009 | Lim et al. | |
| 7,585,311 B2 | 9/2009 | Green et al. | |
| 7,766,208 B2 | 8/2010 | Epperly et al. | |
| 7,771,440 B2 | 8/2010 | Ortiz et al. | |
| 7,776,057 B2 | 8/2010 | Laufer et al. | |
| 7,780,685 B2 | 8/2010 | Hunt et al. | |
| 7,785,255 B2 | 8/2010 | Malkani | |
| 7,807,192 B2 | 10/2010 | Li et al. | |
| 7,819,880 B2 | 10/2010 | Zannis et al. | |
| 7,918,879 B2 | 4/2011 | Yeung et al. | |
| 8,114,101 B2 | 2/2012 | Criscuolo et al. | |
| 8,197,837 B2 | 6/2012 | Jamiolkowski et al. | |
| 2002/0068936 A1* | 6/2002 | Burkus | A61B 17/025 606/57 |
| 2002/0077687 A1 | 6/2002 | Ahn | |
| 2002/0090725 A1 | 7/2002 | Simpson et al. | |
| 2002/0123767 A1 | 9/2002 | Prestel | |
| 2002/0165559 A1 | 11/2002 | Grant et al. | |
| 2003/0073979 A1 | 4/2003 | Naimark et al. | |
| 2003/0125749 A1 | 7/2003 | Li et al. | |
| 2003/0212456 A1 | 11/2003 | Lipchitz et al. | |
| 2004/0059416 A1 | 3/2004 | Murray et al. | |
| 2004/0138705 A1 | 7/2004 | Heino et al. | |
| 2004/0167519 A1 | 8/2004 | Weiner et al. | |
| 2005/0015021 A1 | 1/2005 | Shiber | |
| 2005/0049618 A1 | 3/2005 | Masuda et al. | |
| 2005/0051597 A1 | 3/2005 | Toledano | |
| 2005/0059996 A1 | 3/2005 | Bauman et al. | |
| 2005/0060033 A1 | 3/2005 | Vacanti et al. | |
| 2005/0107807 A1 | 5/2005 | Nakao | |
| 2005/0113736 A1 | 5/2005 | Orr et al. | |
| 2005/0171569 A1 | 8/2005 | Girard et al. | |
| 2005/0187576 A1 | 8/2005 | Whitman et al. | |
| 2005/0240222 A1 | 10/2005 | Shipp | |
| 2005/0240259 A1* | 10/2005 | Sisken | A61F 2/02 623/1.36 |
| 2005/0274768 A1 | 12/2005 | Cummins et al. | |
| 2006/0074423 A1 | 4/2006 | Alleyne et al. | |
| 2006/0178743 A1 | 8/2006 | Carter | |
| 2006/0235442 A1 | 10/2006 | Huitema | |
| 2006/0293760 A1 | 12/2006 | DeDeyne | |
| 2007/0078477 A1 | 4/2007 | Heneveld, Sr. et al. | |
| 2007/0083236 A1 | 4/2007 | Sikora et al. | |
| 2007/0112361 A1 | 5/2007 | Schonholz et al. | |
| 2007/0179531 A1 | 8/2007 | Thornes | |
| 2007/0185506 A1 | 8/2007 | Jackson | |
| 2007/0190108 A1 | 8/2007 | Datta et al. | |
| 2007/0219558 A1 | 9/2007 | Deutsch | |
| 2007/0270804 A1 | 11/2007 | Chudik | |
| 2007/0288023 A1 | 12/2007 | Pellegrino et al. | |
| 2008/0027470 A1 | 1/2008 | Hart et al. | |
| 2008/0051888 A1 | 2/2008 | Ratcliffe et al. | |
| 2008/0065153 A1 | 3/2008 | Allard et al. | |
| 2008/0090936 A1 | 4/2008 | Fujimura et al. | |
| 2008/0125869 A1 | 5/2008 | Paz et al. | |
| 2008/0135600 A1 | 6/2008 | Hiranuma et al. | |
| 2008/0173691 A1 | 7/2008 | Mas et al. | |
| 2008/0188874 A1 | 8/2008 | Henderson | |
| 2008/0188936 A1 | 8/2008 | Ball et al. | |
| 2008/0195119 A1 | 8/2008 | Ferree | |
| 2008/0200949 A1 | 8/2008 | Hiles et al. | |
| 2008/0241213 A1 | 10/2008 | Chun et al. | |
| 2008/0272173 A1 | 11/2008 | Coleman et al. | |
| 2008/0306408 A1 | 12/2008 | Lo | |
| 2009/0001122 A1 | 1/2009 | Prommersberger et al. | |
| 2009/0012521 A1 | 1/2009 | Axelson, Jr. et al. | |
| 2009/0030434 A1 | 1/2009 | Paz et al. | |
| 2009/0069806 A1 | 3/2009 | De La Mora Levy et al. | |
| 2009/0076541 A1 | 3/2009 | Chin et al. | |
| 2009/0105535 A1 | 4/2009 | Green et al. | |
| 2009/0112085 A1 | 4/2009 | Eby | |
| 2009/0118734 A1* | 5/2009 | Bhatnagar | A61B 17/064 606/75 |
| 2009/0134198 A1 | 5/2009 | Knodel et al. | |
| 2009/0156986 A1 | 6/2009 | Trenhaile | |
| 2009/0156997 A1 | 6/2009 | Trenhaile | |
| 2009/0182245 A1 | 7/2009 | Zambelli | |
| 2009/0242609 A1 | 10/2009 | Kanner | |
| 2010/0145367 A1 | 6/2010 | Ratcliffe | |
| 2010/0147922 A1 | 6/2010 | Olson | |
| 2010/0163598 A1 | 7/2010 | Belzer | |
| 2010/0191332 A1 | 7/2010 | Euteneuer et al. | |
| 2010/0241227 A1 | 9/2010 | Euteneuer et al. | |
| 2010/0249801 A1 | 9/2010 | Sengun et al. | |
| 2010/0256675 A1 | 10/2010 | Romans | |
| 2010/0274278 A1 | 10/2010 | Fleenor et al. | |
| 2010/0292715 A1 | 11/2010 | Nering et al. | |
| 2010/0292791 A1 | 11/2010 | Lu et al. | |
| 2010/0312250 A1 | 12/2010 | Euteneuer et al. | |
| 2010/0312275 A1 | 12/2010 | Euteneuer et al. | |
| 2010/0327042 A1 | 12/2010 | Amid et al. | |
| 2011/0000950 A1 | 1/2011 | Euteneuer et al. | |
| 2011/0004221 A1 | 1/2011 | Euteneuer et al. | |
| 2011/0011917 A1 | 1/2011 | Loulmet | |
| 2011/0034942 A1 | 2/2011 | Levin et al. | |
| 2011/0040310 A1 | 2/2011 | Levin et al. | |
| 2011/0040311 A1 | 2/2011 | Levin et al. | |
| 2011/0066166 A1 | 3/2011 | Levin et al. | |
| 2011/0106154 A1 | 5/2011 | DiMatteo et al. | |
| 2011/0114700 A1 | 5/2011 | Baxter, III et al. | |
| 2011/0224702 A1 | 9/2011 | Van Kampen et al. | |
| 2011/0264149 A1 | 10/2011 | Pappalardo et al. | |
| 2012/0100200 A1 | 4/2012 | Belcheva et al. | |
| 2012/0160893 A1 | 6/2012 | Harris et al. | |
| 2012/0193391 A1 | 8/2012 | Michler et al. | |
| 2012/0209401 A1 | 8/2012 | Euteneuer et al. | |
| 2012/0211543 A1 | 8/2012 | Euteneuer | |
| 2012/0248171 A1 | 10/2012 | Bailly et al. | |
| 2012/0316608 A1 | 12/2012 | Foley | |
| 2013/0153627 A1 | 6/2013 | Euteneuer et al. | |
| 2013/0153628 A1 | 6/2013 | Euteneuer | |
| 2013/0158554 A1 | 6/2013 | Euteneuer et al. | |

(56) References Cited

U.S. PATENT DOCUMENTS

| | | |
|---|---|---|
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |
| EP | 2030576 A2 | 3/2009 |
| GB | 2154688 A | 9/1985 |
| GB | 2397240 A | 7/2004 |
| JP | 58188442 A | 11/1983 |
| JP | 2005506122 A | 3/2005 |
| JP | 2006515774 A | 6/2006 |
| WO | 8505025 A1 | 11/1985 |
| WO | 0176456 A2 | 10/2001 |
| WO | 0234140 A2 | 5/2002 |
| WO | 03105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2010141872 A1 | 12/2010 |
| WO | 2011095890 A2 | 8/2011 |
| WO | 2011128903 A2 | 10/2011 |

OTHER PUBLICATIONS

Chamay et al., "Digital Contracture Deformity After Implantation of a Silicone Prosthesis: Light and Electron Microscopic Study", The Journal of Hand Surgery, vol. 3, No. 3, pp. 266-270, May 1978.

D'ermo et al., "Our Results with the Operation of Ab Externo", Ophthalmologica, vol. 168, pp. 347-355, (year of publication sufficiently earlier than effective U.S. filing date and any foreign priority date), 1971.

France et al., "Biomechanical Evaluation of Rotator Cuff Fixation Methods", The American Journal of Sports Medicine, vol. 17, No. 2, pp. 176-181, Mar.-Apr. 1989.

Goodship et al., "An Assessment of Filamentous Carbon Fibre for the Treatment of Tendon Injury in the Horse", Veterinary Record, vol. 106, pp. 217-221, Mar. 8, 1980.

Hunter et al., "Flexor-Tendon Reconstruction in Severely Damaged Hands", The Journal of Bone and Joint Surgery American Volume), vol. 53-A, No. 5, pp. 329-358, Jul. 1971.

Johnstone et al., "Microsurgery of Schlemm's Canal and the Human Aqueous Outflow System", American Journal Opthalmology, vol. 76, No. 6, pp. 906-917, Dec. 1973.

Kowalsky et al., "Evaluation of Suture Abrasion Against Rotator Cuff Tendon and Proximal Humerus Bone", Arthroscopy: The Journal of Arthroscopic and Related Surgery, vol. 24, No. 3, pp. 329-334, Mar. 2008.

Lee et al., "Aqueous-Venous and Intraocular Pressure. Preliminary Report of Animal Studies", Investigative Ophthalmology, vol. 5, No. 1, pp. 59-64, Feb. 1966.

Maepea et al., "The Pressures in the Episcleral Veins, Schlemm's Canal and the Trabecular Meshwork in Monkeys: Effects of Changes in Intraocular Pressure", Exp. Eye Res., vol. 49, pp. 645-663, Oct. 1989.

Nicolle et al., "A Silastic Tendon Prosthesis as an Adjunct to Flexor Tendon Grafting . . . ", British Journal of Plastic Surgery, 22 (3-4), pp. 224-236, (year of publication sufficiently earlier than effective U.S. filing date and any foreign priority date), 1969.

Rubin et al., "The Use of Acellular Biologic Tissue Patches in Foot and Ankle Surgery", Clinics in Podiatric Medicine and Surgery, vol. 22, pp. 533-552, Oct. 2005.

Schultz, "Canaloplasty Procedure Shows Promise for Open-Angle Glaucoma in European Study", Ocular Surgery Mews, pp. 34-35, Mar. 1, 2007.

Spiegel et al., "Schlemm's Canal Implant: A New Method to Lower Intraocular Pressure in Patients with POAG", Ophthalmic Surgery and Lasers, vol. 30, No. 6, pp. 492-494, Jun. 1999.

Stetson et al., "Arthroscopic Treatment of Partial Rotator Cuff Tears", Operative Techniques in Sports Medicine, vol. 12, Issue 2, pp. 135-148, Apr. 2004.

Valdez et al., "Repair of Digital Flexor Tendon Lacerations in the Horse, Using Carbon Fiber Implants", JAYMA, vol. 177, No. 5, pp. 427-435, Sep. 1, 1980.

Wikipedia, The Free Encyclopedia, "Rotator Cuff Tear", downloaded from <http://en.wikipedia.org/wiki/Rotator_cuff_tear, 14 pages, Dec. 6, 2012.

Euteneuer et al., U.S. Appl. No. 13/889,675 entitled "Methods and Apparatus for Fixing Sheet-Like Materials to a Target Tissue", filed May 8, 2013.

Euteneuer et al., U.S. Appl. No. 13/889,687 entitled "Methods and Apparatus for Delivering Staples to a Target Tissue", filed May 8, 2013.

Van Kampen et al., U.S. Appl. No. 13/889,701 entitled "Tendon Repair Implant and Method of Arthroscopic Implantation", filed May 8, 2013.

Euteneuer et al., U.S. Appl. No. 13/889,737 entitled "Fasteners and Fastener Delivery Devices for Affixing Sheet-Like Materials to Bone or Tissue", filed May 8, 2013.

Euteneuer et al., U.S. Appl. No. 13/889,757 entitled "Methods and Apparatus for Delivering and Positioning Sheet-Like Materials in Surgery", filed May 8, 2013.

Euteneuer et al., U.S. Appl. No. 13/889,774 entitled "Guidewire Having a Distal Fixation Member for Delivering and Positioning Sheet-Like Materials in Surgery", filed May 8, 2013.

Euteneuer et al., U.S. Appl. No. 13/889,832 entitled "ANatomical Location Markers and Methods of Use in Positioning Sheet-Like Materials During Surgery", filed May 8, 2013.

Alexander et al., "Ligament and tendon repair with an absorbable polymer-coated carbon fiber stent", Bulletin of the Hospital for Joint Diseases Orthopaedic Institute, vol. 46(2), pp. 155-173, Fall 1986.

\* cited by examiner

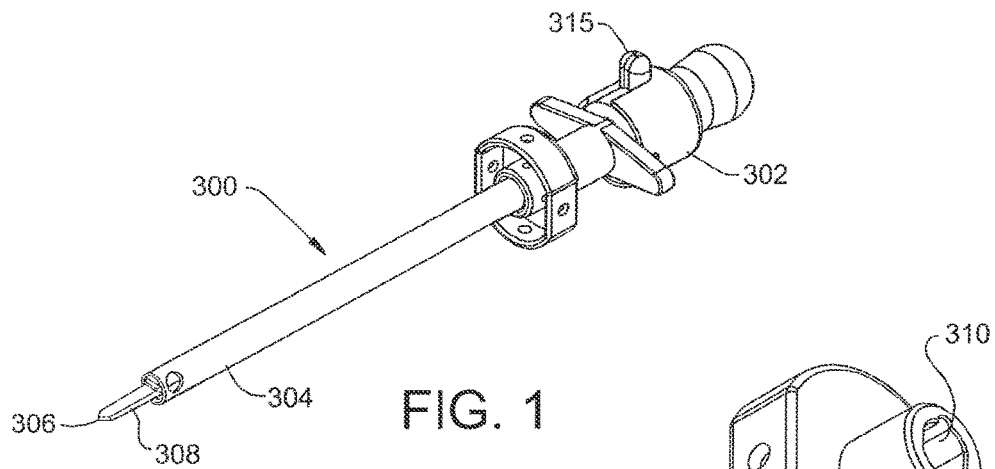
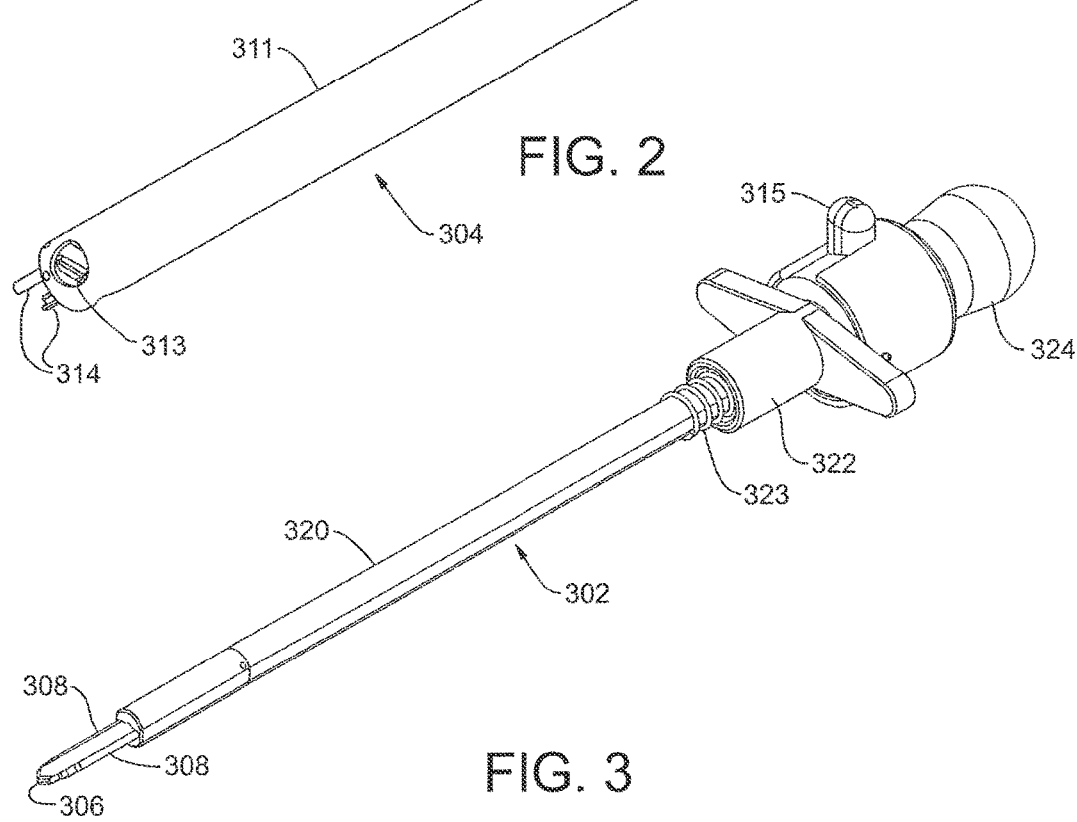

APPARATUS AND METHOD FOR FORMING PILOT HOLES IN BONE AND DELIVERING FASTENERS THEREIN FOR RETAINING AN IMPLANT

CROSS REFERENCE TO RELATED APPLICATIONS

This application is a continuation of U.S. application Ser. No. 13/889,722, filed May 8, 2013, which is a continuation of U.S. application Ser. No. 13/717,474, filed Dec. 17, 2012, which claims the benefit of U.S. Provisional Patent Application Ser. No. 61/577,621 filed on Dec. 19, 2011, the disclosures of each incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to orthopedic medicine and surgery. More particularly, the present invention relates to methods and apparatus for forming pilot holes in bone for inserting fasteners and fixation of sheet-like materials, such as for treating tendons or like tissue of articulating joints, such as tendons in the rotator cuff of the shoulder.

BACKGROUND OF THE INVENTION

The glenohumeral joint of the shoulder is found where the head of the humerus mates with a shallow depression in the scapula. This shallow depression is known as the glenoid fossa. Six muscles extend between the humerus and scapula and actuate the glenohumeral joint. These six muscles include the deltoid, the teres major, and the four rotator cuff muscles. The rotator cuff muscles are a complex of muscles. The muscles of the rotator cuff include the supraspinatus, the infraspinatus, the subscapularis, and the teres minor. The centering and stabilizing roles played by the rotator cuff muscles are critical to the proper function of the shoulder. The rotator cuff muscles provide a wide variety of moments to rotate the humerus and to oppose unwanted components of the deltoid and pectoral muscle forces.

The muscles of the rotator cuff arise from the scapula. The distal tendons of the rotator cuff muscles splay out and interdigitate to form a common continuous insertion on the humerus. The supraspinatus muscle arises from the supraspinatus fossa of the posterior scapula, passes beneath the acromion and the acromioclavicular joint, and attaches to the superior aspect of the greater tuberosity. The mechanics of the rotator cuff muscles are complex. The rotator cuff muscles rotate the humerus with respect to the scapula, compress the humeral head into the glenoid fossa providing a critical stabilizing mechanism to the shoulder (known as concavity compression), and provide muscular balance. The supraspinatus and deltoid muscles are equally responsible for producing torque about the shoulder joint in the functional planes of motion.

The rotator cuff muscles are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear at the insertion site of the tendon with the humerus, may result in the detachment of the tendon from the bone. This detachment may be partial or full, depending upon the severity of the injury or damage. Additionally, the strain or tear can occur within the tendon itself. Injuries to the supraspinatus tendon and current modalities for treatment are defined by the type and degree of tear. The first type of tear is a full thickness tear, which as the term indicates is a tear that extends through the thickness of the supraspinatus tendon regardless of whether it is completely torn laterally. The second type of tear is a partial thickness tear which is further classified based on how much of the thickness is torn, whether it is greater or less than about 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In contrast to the treatment of a full thickness tear or a partial thickness tear of greater than 50%, the current standard treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause restricted use of the limb which tends to result in further degeneration or atrophy in the shoulder.

Surgical intervention may be required for a partial thickness tear of less than 50%, however, current treatment interventions do not include repair of the tendon, and rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is ablated. Again, the tendon partial thickness tear is not repaired. Several authors have reported satisfactory early post operative results from these procedures, but over time recurrent symptoms have been noted. In the event of recurrent symptoms, many times a patient will "live with the pain". This may result in less use of the arm and shoulder which causes further degeneration of the tendon and may lead to more extensive damage. A tendon repair would then need to be done in a later procedure if the prescribed treatment for the partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. Further, it would be beneficial to be able to treat partial thickness tears greater than 50% without cutting the untorn portion of the tendon to complete the tear before suturing back together. There is a large need for surgical techniques and systems to treat partial thickness tears and prevent future tendon damage by strengthening or repairing the native tendon having the partial thickness tear.

SUMMARY OF THE DISCLOSURE

The present disclosure is generally directed to an arthroscopic apparatus and method to form pilot holes in bone and retain instrument position relative to formed pilot holes such that a fastener may be delivered into the pilot holes for retention therein. The fastener can be used to fix a sheet-like material or implant to bone in a procedure to place such implant over damaged tendon in an articulating joint, such as the rotator cuff.

In some embodiments, the apparatus generally includes a pilot hole forming trocar assembly having a position retention sleeve and a trocar slidably disposed therein. The position retention sleeve can have a lumen extending therethrough and at least one position retention member proximate a distal end of the position retention sleeve. The trocar can be sized for being releasably disposed within the lumen of the position retention sleeve and can include at least one distally extending spike. When assembled for use, the at least one distally extending spike can extend beyond the distal end of the position retention sleeve to form a pilot hole when contacted with bone.

The pilot hole forming trocar can be included in a kit that further includes a staple delivery device. The staple delivery device can include a barrel sized for disposition within the lumen of the position retention sleeve and delivery of a staple from a distal portion thereof. The barrel can be keyed for controlled rotational relationship of the barrel relative to the position retention sleeve.

In some embodiments, the trocar can include a collar for releasably coupling the trocar to the position retention sleeve. Further, a proximal knob portion having a surfacing for pounding the at least one spike into bone can be included on the trocar. A retractable blade for accessing an incision site can also be included on a distal end of the trocar.

The position retention sleeve can include a plurality of position retention members. The position retention members can include a semi-cylindrical member defining a longitudinal channel over the length thereof that is sized to allow the at least one spike of the trocar to be disposed in the channel during use. In some embodiments, the pilot hole forming trocar assembly includes two spikes and two position retention members to foam pilot holes and retain position to allow inserting a staple having a bridge and two arms into the formed pilot holes.

In a method for fixing a positioned sheet-like material to bone, a position retention sleeve is provided having a lumen extending therethrough and at least one position retention member proximate a distal end of the position retention sleeve. A trocar sized for being releasably disposed within the lumen of the position retention sleeve and including at least one distally extending spike is also provided.

The trocar may be positioned within the position retention sleeve with the at least one spike extending beyond the distal end of the position retention sleeve. The spike may then be driven into the bone to form at least one pilot hole. The trocar may then be removed with the position retention member maintaining the sleeve position relative to the formed pilot hole or holes.

A staple delivery device is provided having a barrel sized for disposition within the lumen of the position retention sleeve. The barrel can be keyed for controlled rotational position of the barrel relative to the position retention sleeve. The staple delivery barrel may then be inserted into the sleeve lumen and the staple deployed.

BRIEF DESCRIPTION OF THE DRAWINGS

The novel FIG. 1 is a simplified perspective view of a pilot hole forming trocar assembly, including a trocar disposed within a position retention sleeve for creating pilot holes and retaining the sleeve relative to the formed pilot holes for delivery of a tissue fastener or staple;

FIG. 2 is a perspective view of the position retention sleeve of FIG. 1 with the trocar removed;

FIG. 3 is a perspective view of the trocar of FIG. 1 as removed from the position retention sleeve;

DETAILED DESCRIPTION OF THE INVENTION

Figure 4A:
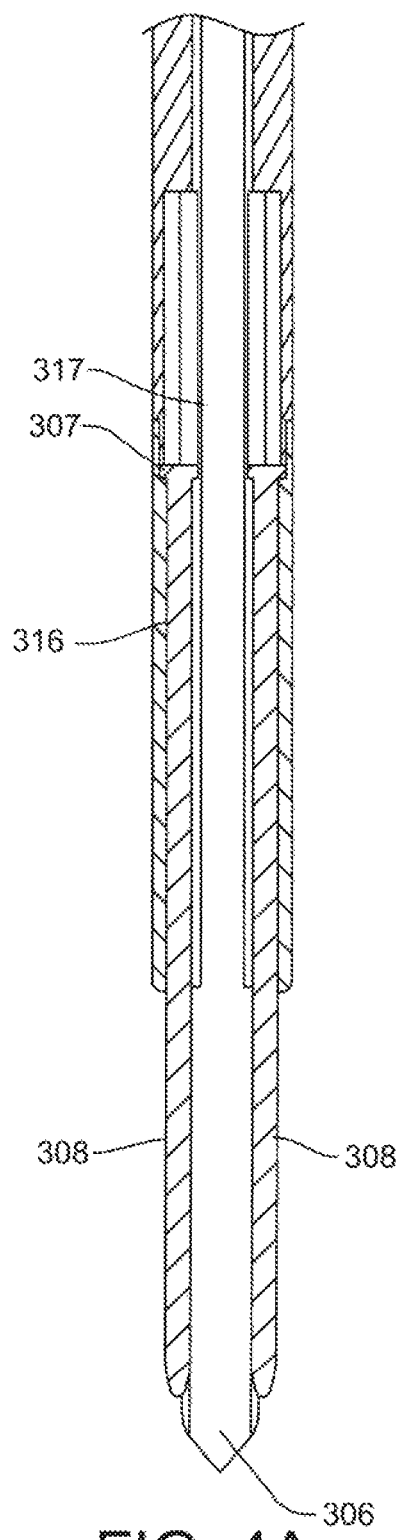
FIGS. 4A and 4B are partial cross sectional views of the distal portion of the trocar of FIG. 3 depicting pilot hole forming spikes and a retractable blade.

The following detailed description should be read with reference to the drawings in which similar elements in different drawings are numbered the same. The drawings, which are not necessarily to scale, depict illustrative embodiments and are not intended to limit the scope of the invention.

Apparatus and methods as described in this disclosure can be used to position and deploy fasteners or staples to attach tissue and implants to bone. In at least some applications, the staple is generally flexible and include a pair of arms connected by a bridge with the arms having trunk portions thereon. Staples can include those disclosed in co-pending applications U.S. Provisional Application No. 61/577,626 filed on Dec. 19, 2011, entitled, "FASTENERS AND FASTENER DELIVERY DEVICES FOR AFFIXING SHEET-LIKE MATERIALS TO BONE OR TISSUE"; U.S. Provisional Application No. 61/577,632 filed on Dec. 19, 2011, entitled, "FASTENERS AND FASTENER DELIVERY DEVICES FOR AFFIXING SHEET-LIKE MATERIALS TO BONE OR TISSUE" and U.S. Provisional Application No. 61/577,635 filed on Dec. 19, 2011, entitled, "FASTENERS AND FASTENER DELIVERY DEVICES FOR AFFIXING SHEET-LIKE MATERIALS TO BONE OR TISSUE," the disclosures of which are incorporated herein by reference. The trunk portions can include areas of relative lateral weakness and can further include an increase in flexibility at the transition from the trunk to the non-trunk portion of the arm or the transition from the trunk to the bridge. These areas of flexibility can provide improved staple retention as these portions allow flexing and bending in response to increasing pullout forces. With this flexibility, the fasteners cannot be pounded or driven into bone or other tissue as a conventional hard staple would be driven into paper, wood, tissue or bone. Therefore, for application of the staple of the present disclosure to affixing tissue or implants to bone, the staples are generally included in a kit that also includes a staple delivery device 200 (generally illustrated in FIG. 6) and a pilot hole forming trocar assembly 300, as schematically illustrated in FIGS. 1-5 and described in detail below.

The pilot hole forming trocar assembly 300, illustrated generally in FIG. 1 includes a trocar 302 and a position retention sleeve 304. The trocar 302 is releasably coupled to the position retention sleeve 304 and slides in keyed arrangement within the sleeve 304 when uncoupled. The trocar 302 includes a distal portion having a retractable blade 306 and a pair of pilot hole forming spikes 308 extending distally from the trocar shaft. The retractable blade 306 is useful in inserting the assembly through an incision. The retractable blade 306 can be retracted by activating release button 315 which causes a spring (not shown) to pull the retractable blade 306 into the shaft of the trocar within the position retention sleeve 304. In this position, the pilot hole forming spikes remain extended from the trocar. In some embodiments the retractable blade 306 can be omitted, such as when the pilot hole forming trocar assembly is to be inserted into an incision that already has a cannula extending therethrough to provide an instrument path.

Referring to FIGS. 2-5, details of the elements of one exemplary embodiment of a pilot hole forming trocar assembly 300 are illustrated. The pilot hole forming trocar assembly 300 is used to create pilot holes in a bone for subsequent placement of a staple or fastener. Further, the pilot hole forming trocar assembly 300 includes a means for retaining instrument position with respect to the pilot holes when the trocar is removed so that a staple delivery device 200 (see FIG. 6) can be inserted and the staple be in alignment with the already formed pilot holes. This prevents the time and difficulty associated with finding the pilot holes with the staple, which in fact may not be possible for many practitioners.

As previously stated, a pilot hole forming trocar assembly 300 can include a trocar 302 and a position retention sleeve 304. One embodiment of a position retention sleeve 304 is illustrated in FIG. 2. The position retention sleeve 304 includes a shaft 311 having a lumen 310 extending therethrough. The lumen 310 is sized to receive the trocar 302 when used to form pilot holes. The lumen 310 is also sized to receive a staple delivery device 200 when used to position a staple in pilot holes formed in bone. The lumen is shaped or keyed to cooperate with either of these instruments or other instruments so that relative rotational position of the trocar 302 or staple delivery device 200 is fixed when slidably positioned in the position retention sleeve 304. An opening or window 313 may be included near the distal end of the position retention sleeve to allow viewing of devices inserted therein.

Position retention members 314 extend distally from the shaft 311. As detailed in FIG. 5, the position retention members can be included on an insert 312 that is affixed proximate the distal end of the shaft 311. Alternatively, the position retention members can be integral to the shaft 311. The position retention members are sized and designed to extend into pilot holes as they are formed by the trocar 302 described below. When the trocar 302 is removed, the position retention members 314, along with the sleeve 311 remain in position to provide a guide for the staple delivery device 200 to be inserted into proper position and position a staple in the pilot holes. As depicted, the position retention members 314 can include longitudinally extending semi-cylindrical projections. In the disclosed embodiment, the pilot hole forming spikes 308 of the trocar 302 slide within the partial lumens of the position retention members 314.

This design can provide support for the spikes as they are pounded into bone and can also allow the position retention members to readily slide into pilot holes formed by the spikes 308.

A more detailed depiction of one alternative embodiment of a trocar 302 is included in FIG. 3. The trocar includes a shaft 320 having at its proximal end a knob 324 that can be used to pound or push the trocar 302 into bone. The trocar can further include a collar 322 which can be used to releasably engage the position retention sleeve 304 when the two are mated for forming pilot holes. A spring 323 can be included which causes or aids the retraction of the trocar when it is released from the position retention sleeve.

Figure 4B:
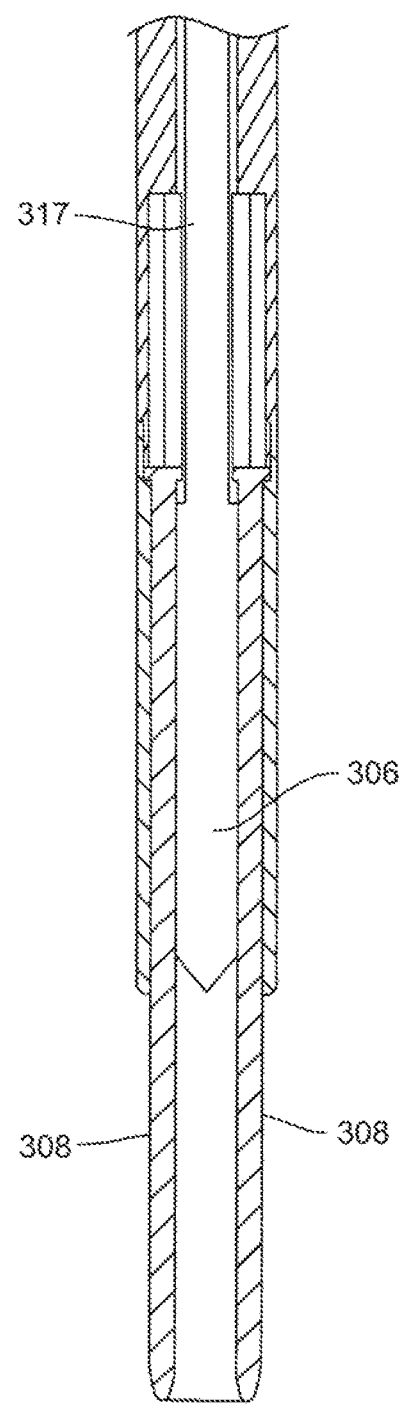
Figure 5:
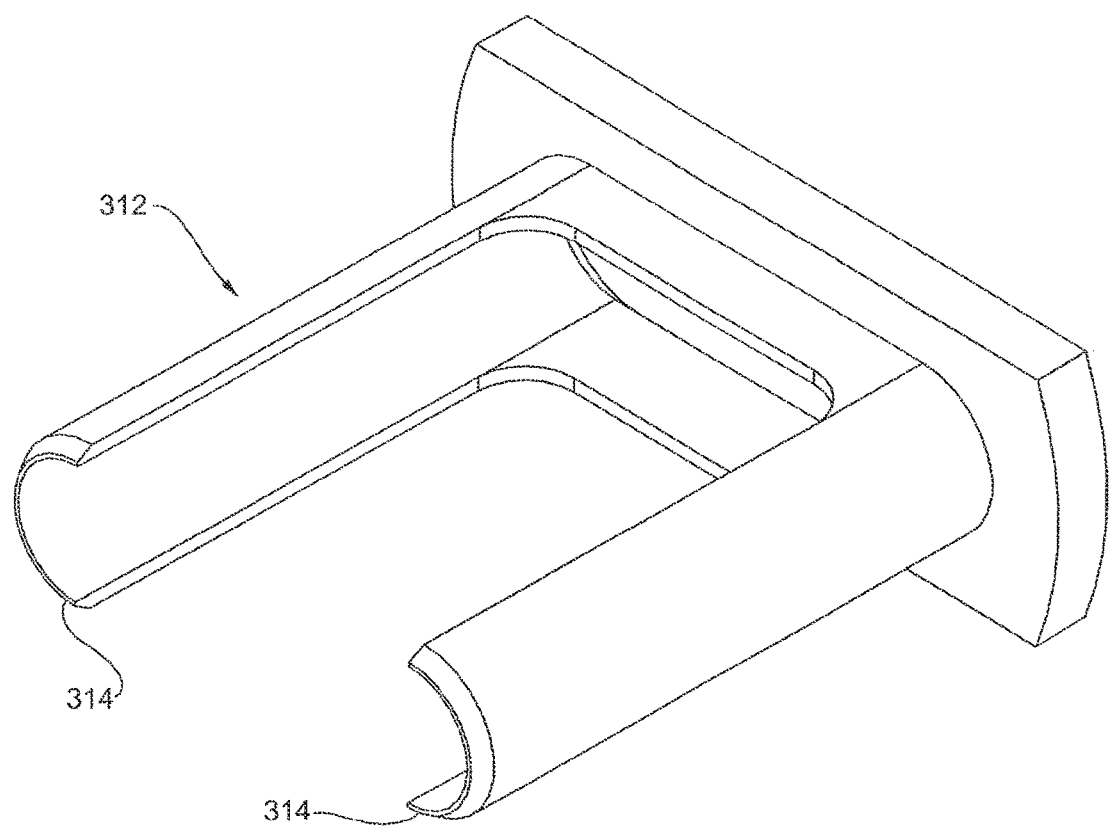
FIG. 5 is a perspective view of a position retention member which can be mounted in a distal portion of the position retention sleeve in one embodiment of the present disclosure.

As previously disclosed, the distal end of the trocar 302 includes two pilot hole forming spikes 308 extending from shaft 320. A retractable blade 306 is positioned between the spikes 308. In use, the blade 306 is retracted prior to the spikes 308 being used to form pilot holes in bone. FIGS. 4A and 4B are a partial cross sectional view of the distal portion of a trocar 302 illustrating the combination of pilot hole forming spikes 308 and a retractable blade 306. The retractable blade 306 includes a proximally extending shaft 317 that is coupled to the previously discussed spring (not shown) and release button 315 which operates to pull the retractable blade into the lumen of the trocar 302. As illustrated, spikes 308 are fixed within lumens 316 in the trocar 302 and extend distally therefrom, for example, the proximal end 307 of spike 308 may be attached to the trocar 302. In FIG. 4A, the blade 306 is shown in an extended position, while in FIG. 4B the blade has been retracted. It is to be understood that spikes 308 are depicted as distally tapering members that can be pounded into bone, however other shapes and configurations are possible within the scope of the invention. For example, spikes 308 could be untapered or have a textured surface. Spikes 308 could also be in the form of rotating bits to effectively drill the pilot holes in some embodiments.

Figure 6A:
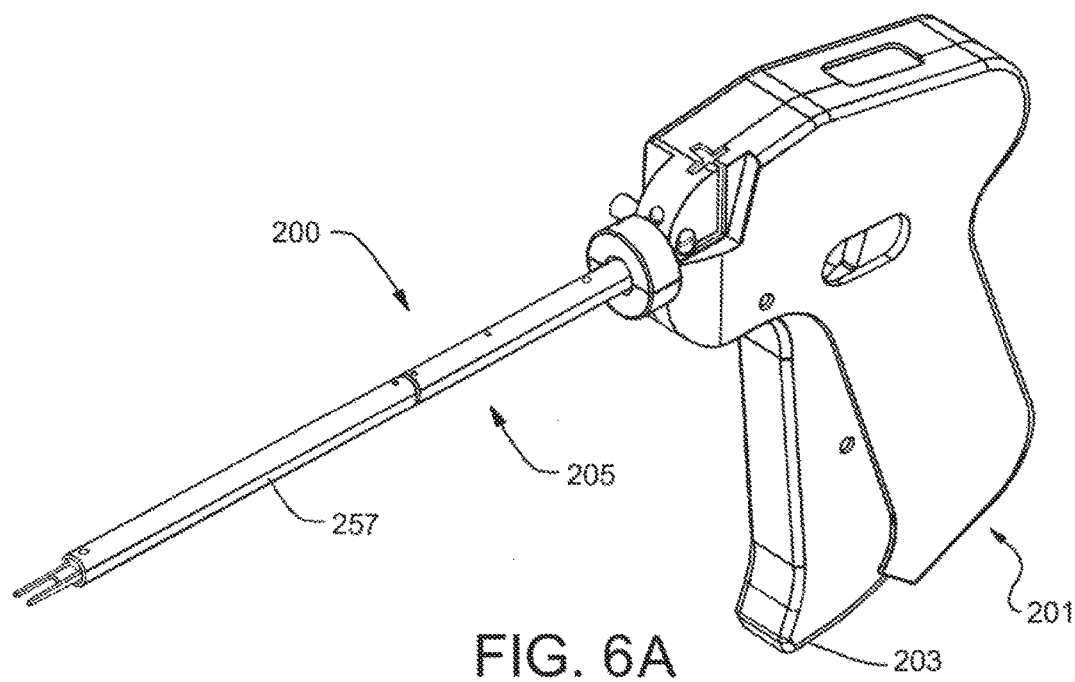
FIG. 6A is a simplified perspective view of a tissue fastener or staple delivery device in accordance with the present disclosure.

Now referring to FIG. 6A, a staple delivery device 200 is illustrated. The staple delivery device 200 can include a handle assembly 201 and a barrel assembly 205. The handle assembly 201 includes a trigger 203 that is operatively coupled to mechanisms in the barrel assembly 205 to deploy a staple in pilot holes formed in bone. The staple delivery device 200 can be used in conjunction with the pilot hole forming trocar assembly 300 of FIG. 1.

Figure 6B:
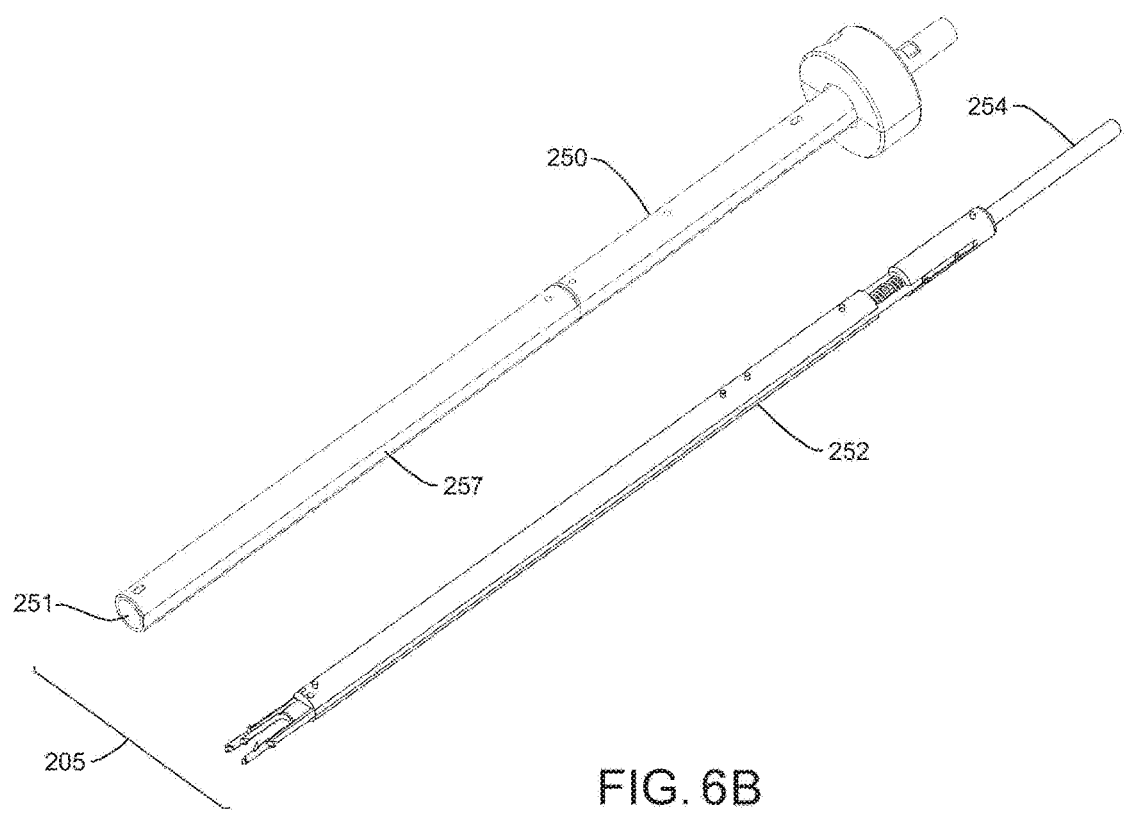
FIG. 6B is a perspective view depicting the sheath and staple pusher assemblies of a staple delivery device in on embodiment of the disclosure.
Figure 6C:
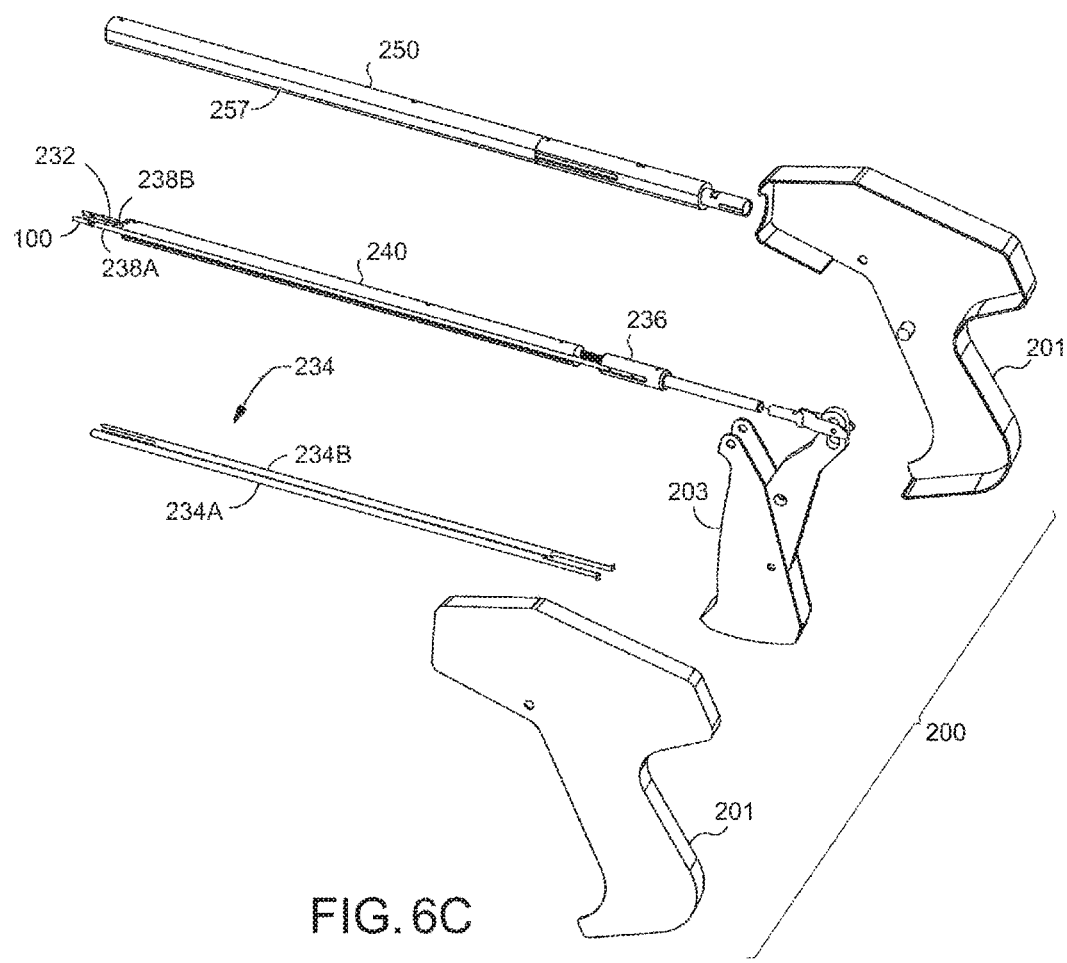
FIG. 6C is a simplified exploded view of the tissue fastener or staple delivery device of FIG. 6A depicting additional features thereof.

The barrel assembly can include two main components, an outer sleeve 250 having a lumen 251 extending therethrough and a staple delivery assembly 252, as depicted in FIG. 6B. The outer sleeve 250 is secured to the handle assembly 201 in fixed relationship when the staple delivery device 200 is assembled. The staple delivery assembly 252 is slidably disposed in the lumen and can include a proximal end 254 extending beyond the proximal end of the outer sleeve 250. The proximal end of the staple delivery assembly 252 operatively interacts with trigger assembly 203 when the barrel 205 is mounted on the handle assembly 201, as can be seen in FIG. 6C. In the embodiment of FIGS. 6A-C, the outer surface of the sleeve 250 is shaped so as to be rotationally keyed and sized for desired fitting within the position retention sleeve 304. As illustrated, the sleeve 250 can include a flat surface 257 keyed to fit within a flat surface on the interior of the position retention sleeve 304.

The staple delivery assembly 252 includes a fork 232, a shaft 240, and two staple setting rods 234. Staple setting rods 234 include a first staple setting rod 234A and a second staple setting rod 234B. Both staple setting rods 234 are affixed to a rod coupler 236 near the proximal end of the staple delivery assembly 252. When the barrel 205 is in an assembled state, first staple setting rod 234A and second staple setting rod 234B can extend through two grooves defined by the outer surface of the staple delivery assembly 252. Each groove is dimensioned so that a staple setting rod can be partially disposed therein while the sleeve 250 surrounds the staple setting rods 234. When staple delivery device 200 is in an assembled state, a staple may be carried by a first stake 238A and a second stake 238B of fork 232.

Figure 7:
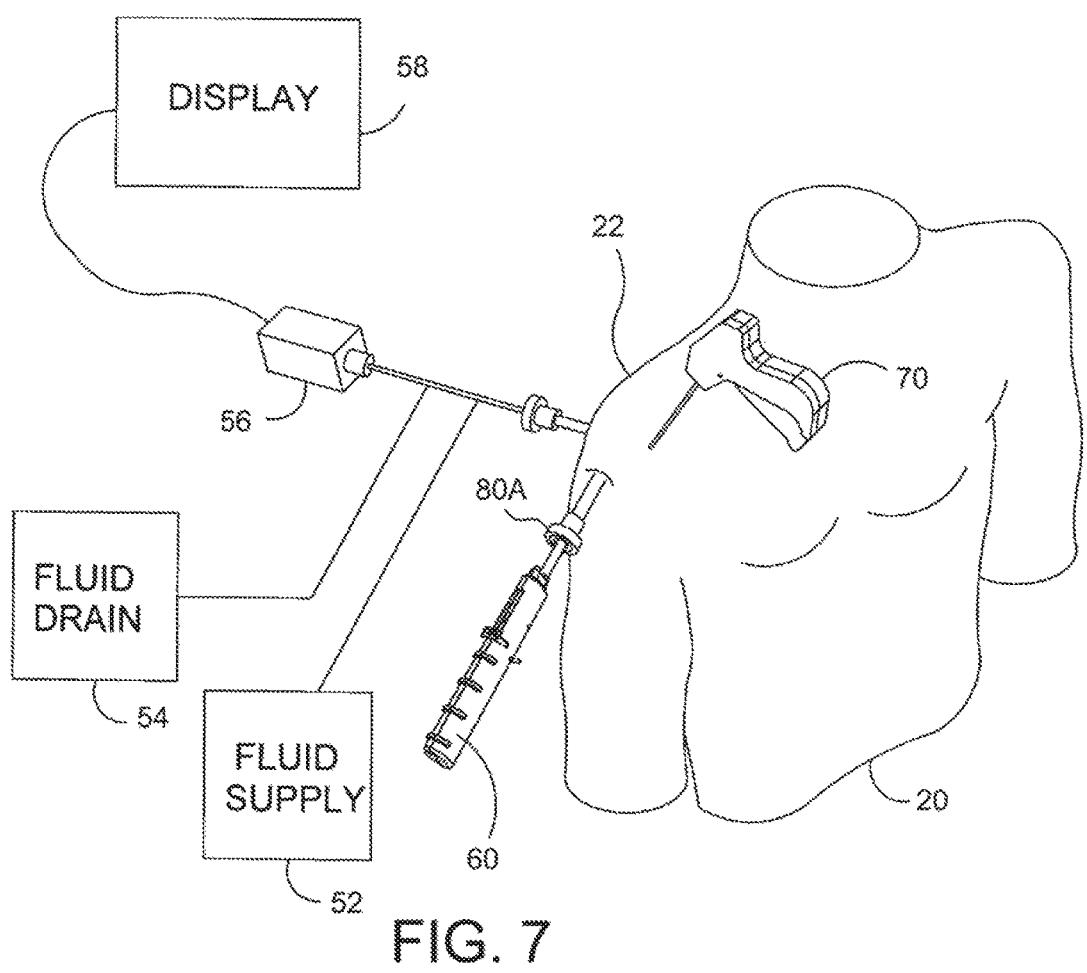
FIG. 7 is a stylized perspective view illustrating an exemplary procedure for arthroscopic treatment of a shoulder of a patient in accordance with one embodiment of the disclosure.

Next referring to FIG. 7, an exemplary use or application of the apparatus of the present disclosure is described. FIG. 7 is a stylized perspective view illustrating an exemplary procedure for treating a shoulder 22 of a patient 20. The procedure illustrated in FIG. 7 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 7 has been inflated to create a cavity therein. A fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be affixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

An implant delivery system 60 can be seen extending from shoulder 22 in FIG. 7. Implant delivery system 60 is extending through a first cannula 80A. In certain embodiments, first cannula 80A can access a treatment site within shoulder 22 using a lateral approach in which first cannula 80A pierces the outer surface of a right side of the patient's body. In some cases a physician may choose not to use a cannula in conjunction with implant delivery system 60. When that is the case, the implant delivery system may be advanced through tissue. Implant delivery system 60 comprises a sheath that is affixed to a handle. The sheath defines a lumen and a distal opening fluidly communicating with the lumen. In the embodiment of FIG. 7, the distal opening of the sheath has been placed in fluid communication with the cavity created in shoulder 22.

A tendon repair implant is at least partially disposed in the lumen defined by the sheath of implant delivery system 60. Implant delivery system 60 can be used to place the tendon repair implant inside shoulder 22. In some embodiments, the tendon repair implant is folded into a compact configuration when inside the lumen of the sheath. When this is the case, implant delivery system 60 may be used to unfold the tendon repair implant into an expanded shape. Additionally, implant delivery system 60 can be used to hold the tendon repair implant against the tendon.

The tendon repair implant may be affixed to the tendon while it is held against the tendon by implant delivery system 60. Various attachment elements may be used to fix the tendon-repair implant to the tendon. Examples of attachment elements that may be suitable in some applications include sutures, tissue anchors, bone anchors, and staples. In the exemplary embodiment of FIG. 7, the shaft of a fixation tool 70 is shown extending into shoulder 22. In one exemplary embodiment, fixation tool 70 is capable of fixing the tendon repair implant to the tendon and bone with one or more staples of the present disclosure while the tendon repair implant may be held against the tendon by implant delivery system 60.

Figure 8:
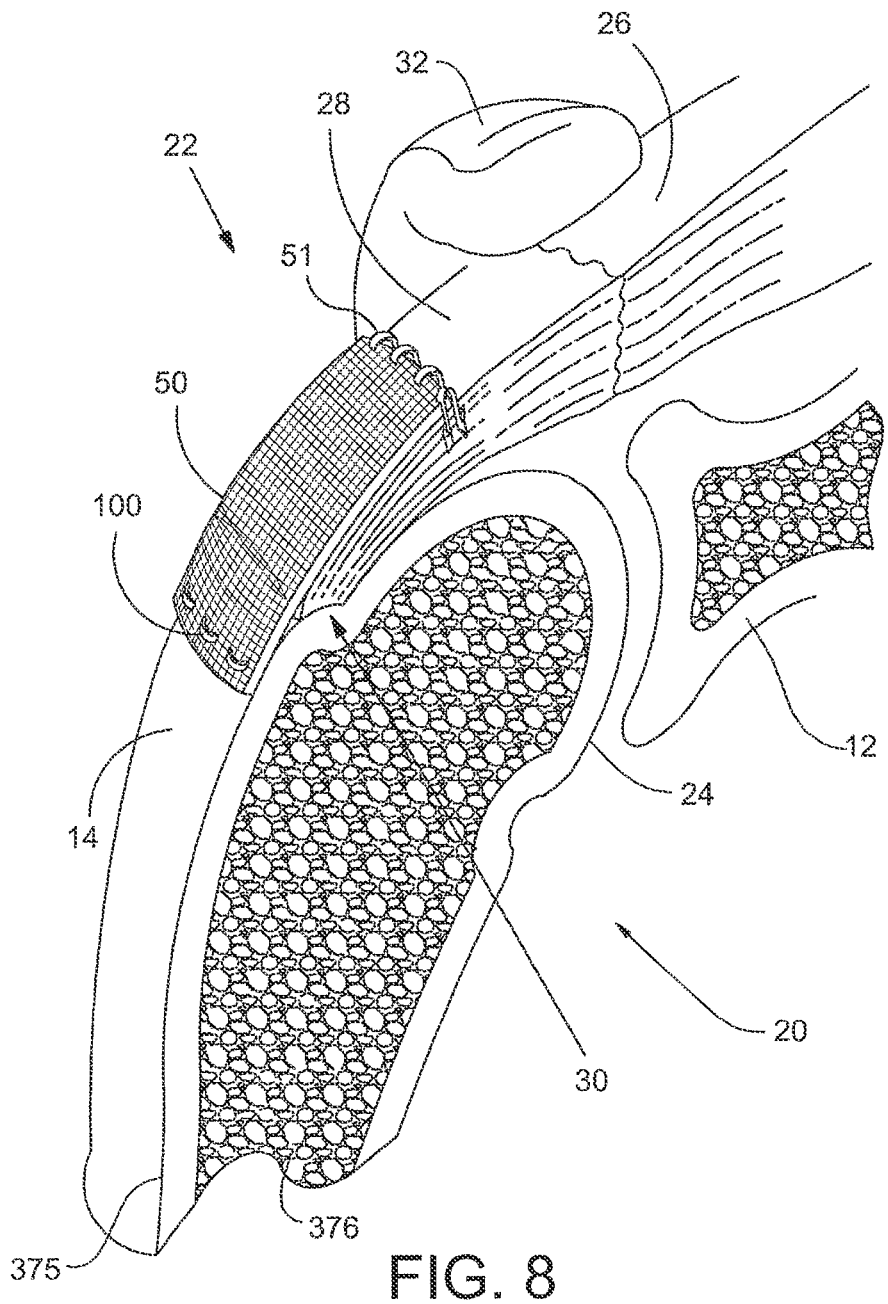
FIG. 8 is a stylized perspective view of a shoulder including a supraspinatus having a distal tendon with a sheet-like material affixed thereto.

For purposes of illustration, a shoulder 22 of patient 20 is shown in cross-section in FIG. 8. Shoulder 22 includes a humerus 14 and a scapula 12. In FIG. 8, a head 24 of humerus 14 can be seen mating with a glenoid fossa of scapula 12 at a glenohumeral joint. The glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 8.

With reference to FIG. 8, a distal tendon 28 of the supraspinatus 26 meets humerus 14 at an insertion point. Scapula 12 of shoulder 22 includes an acromium 32. A tendon repair implant 50 has been affixed to a surface of distal tendon 28. Tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications include weaving, knitting, and braiding. In some embodiments, the sheet-like structure may comprise a laminate including multiple layers of film with each layer of film defining a plurality of micro-machined or formed holes. The sheet-like structure of the tendon repair implant may also comprise a reconstituted collagen material having a porous structure. Additionally, the sheet-like structure of the tendon repair implant may also comprise a plurality of electro-spun nano-fiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Fremont, Calif. which identifies these materials using the trademark BIO-MATERIAL™. The sheet-like structure may be circular, oval, oblong, square, rectangular, or other shape configured to suit the target anatomy.

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the embodiment of FIG. 8, sheet-like implant 50 is affixed to distal tendon 28 by a plurality of tendon staples 51. Sheet-like implant 50 is affixed to humerus 14 by a plurality of bone staples using an apparatus and method of the present disclosure.

In some exemplary methods, a plurality of staples may be applied using a fixation tool. After the staples are applied, the fixation tool may be withdrawn from the body of the patient. Distal tendon 28 meets humerus 14 at an insertion point 30. With reference to FIG. 8, it will be appreciated that sheet-like implant 50 extends over insertion point 30. Tendon repair implant may be applied to distal tendon 28. In various embodiments, staples may straddle the perimeter edge of the sheet-like implant (as shown in FIG. 8), may be applied adjacent to the perimeter, and/or be applied to a central region of the implant. In some embodiments, the staples may be used to attach the implant to soft tissue and/or to bone.

The exemplary apparatus and methods described herein may be used to affix tendon repair implants to various target tissues. The shoulder depicted in FIG. 8 is one example where a tendon repair implant may be affixed to one or more bones associated with an articulating joint, such as the glenohumeral joint. Additionally, the tendon repair implant may be affixed to one or more tendons to be treated. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon-repair implant early before a full tear or other injury develops, the implant may cause the tendon to thicken and/or at least partially repair itself, thereby avoiding more extensive joint damage, pain, and the need for more extensive joint repair surgery.

Figure 9A:
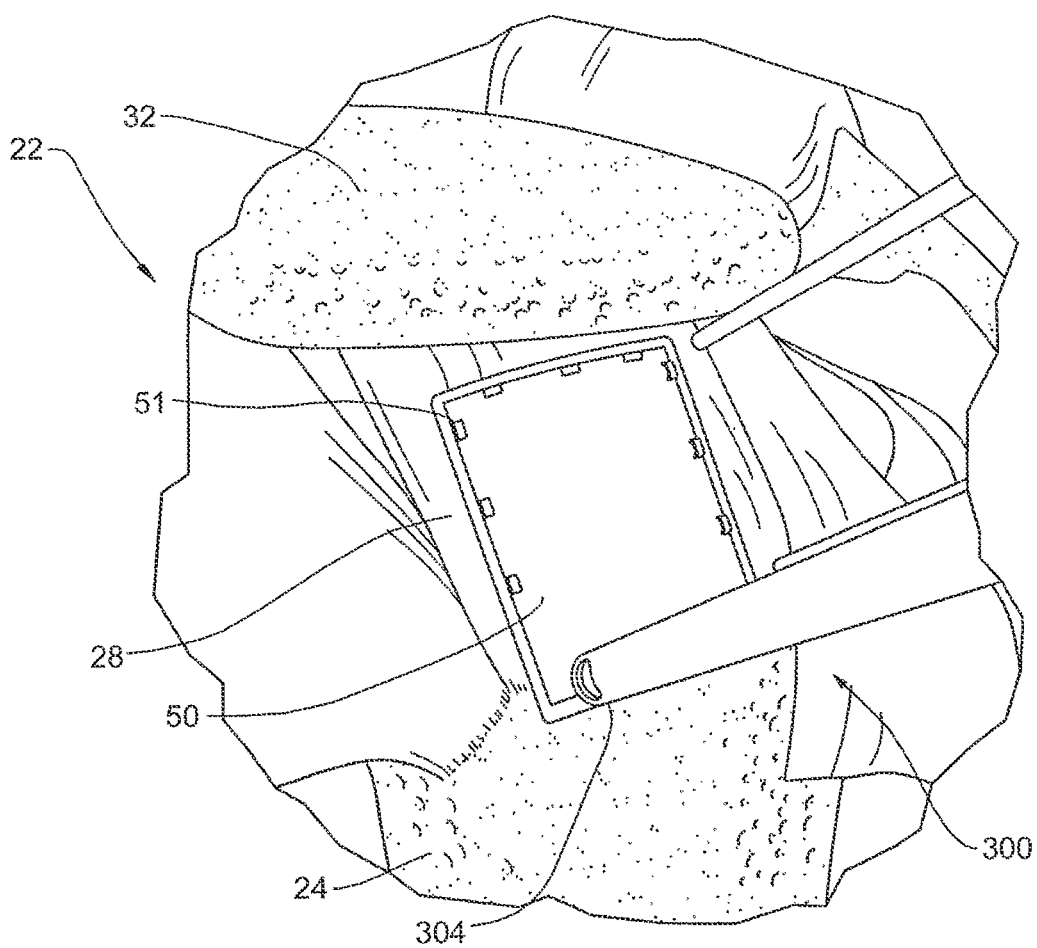
FIG. 9A is simplified perspective view of a shoulder having an implant affixed to the tendon and depicting the first step in a method of delivering fasteners to affix the implant to bone of the humeral head in accordance with one method of the disclosure.

An exemplary method of the present disclosure for forming pilot holes and delivering staples to bone is described with respect to FIGS. 9A-9F which depict the various steps in affixing an implant 50 to bone with staples or fasteners. FIG. 9A schematically depicts a shoulder 22 of a patient 20 having an implant 50 positioned over a supraspinitus tendon 28. The implant is partially affixed to the tendon 28 with fasteners 51 and extends laterally to and over the insertion point of the tendon to the humeral head 24. As depicted, the implant 50 is not yet affixed to the humeral head 24. A distal portion of a pilot hole forming trocar assembly 300, in particular the position retention sleeve 304, is disposed over a desired location near the lateral edge of the implant 50 where it overlies the humeral head 24. It is noted that FIG. 9A is a depiction with all overlying tissue removed from the shoulder 22 to clearly show the location of the entire implant 50 on the supraspinitus tendon 28. This view is typically not possible during actual arthroscopic procedures in which the fasteners and instruments of the present disclosure can be used, however the depiction provides a clear understanding of the placement of an implant and the use of fasteners disclosed herein. In actual use the surgeon will typically have a side view from a viewing scope (not shown) of a small space created by inflating the area with fluid and clearing necessary obstructions from the implant area.

Figure 9B:
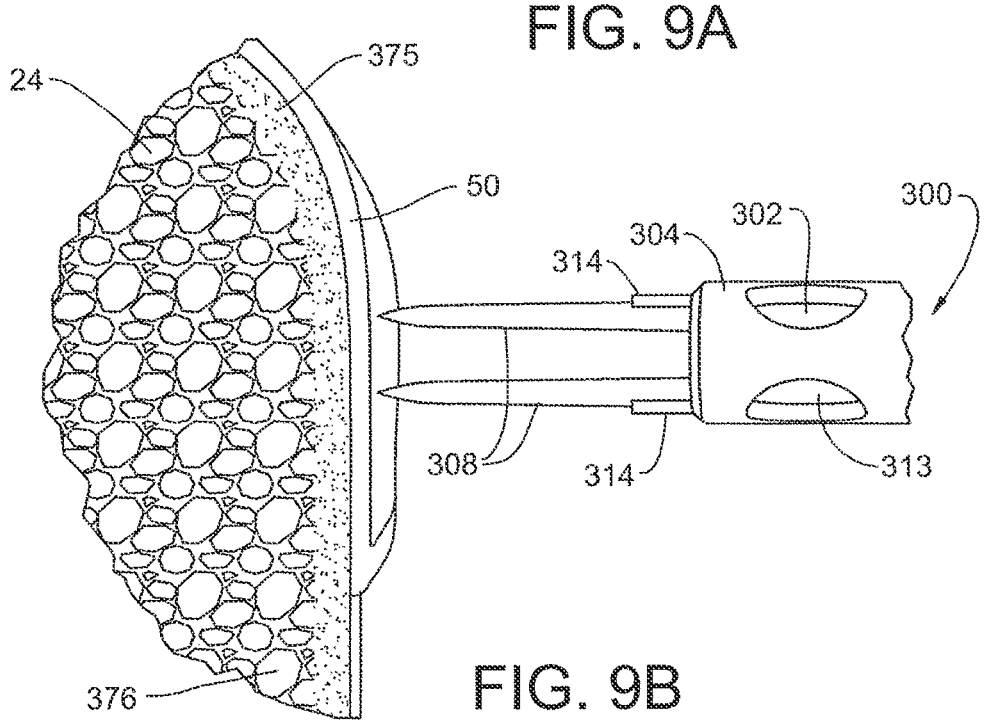
FIG. 9B is a simplified plan view of the distal portion of the trocar assembly as positioned to create pilot holes for affixing the implant to bone in a further step of a method of the disclosure.

FIG. 9B is a schematic illustration of a cross-sectional side view of the partially affixed implant of FIG. 9A showing the small portion of the implant 50 that is not yet affixed to the humeral head 24. As can be seen in the illustration, the humeral head 24 is shown in cross-section which illustrates the composite nature of bone structure. In general, bone includes hard outer portion or cortical layer 375 and a porous softer inner portion or cancellous bone 376. The pilot hole forming trocar assembly 300 is positioned with the spikes 308 over a selected position on the implant 50. As previously discussed, the trocar 302 is positioned within the lumen of the position retention sleeve 304 with spikes 308 extending distally. The spikes 308 can be used to manipulate and position the implant as needed. Once in position, the spikes 308 can be driven into the bone.

Figure 9C:
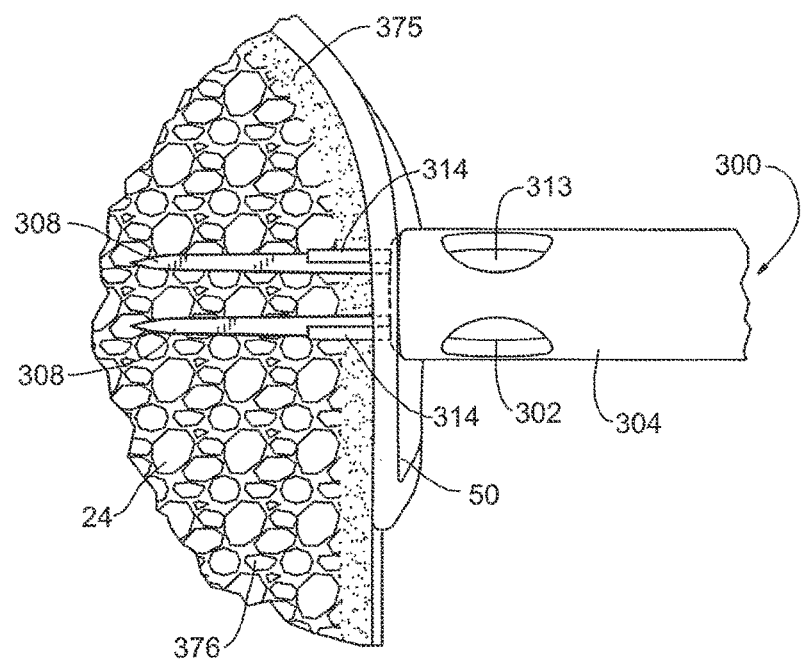
FIG. 9C depicts the trocar assembly of FIG. 9B as inserted into the bone to form pilot holes in accordance with a method of the disclosure.
Figure 9D:
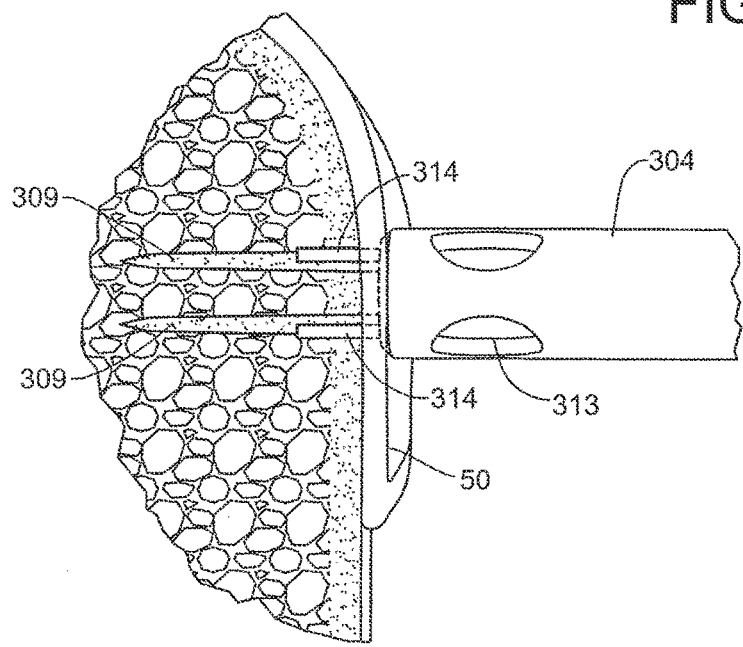
FIG. 9D depicts the trocar assembly with the trocar portion removed and the remaining sheath assembly retaining its position in the pilot holes formed.
Figure 9E:
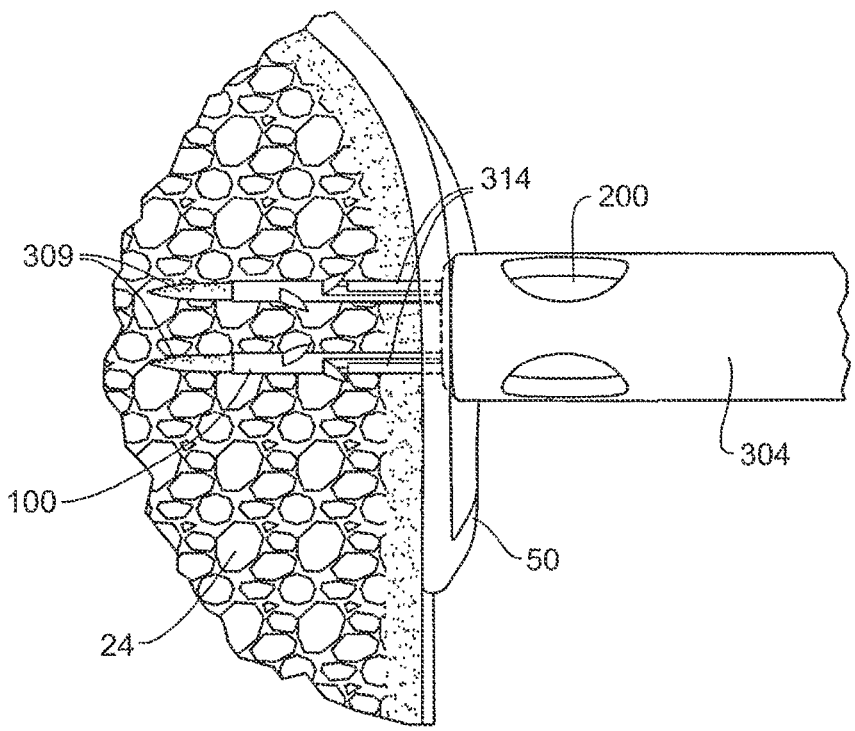
FIG. 9E depicts insertion of a fastener or staple into the formed pilot holes through the sheath assembly in accordance with a method of the disclosure.
Figure 9F:
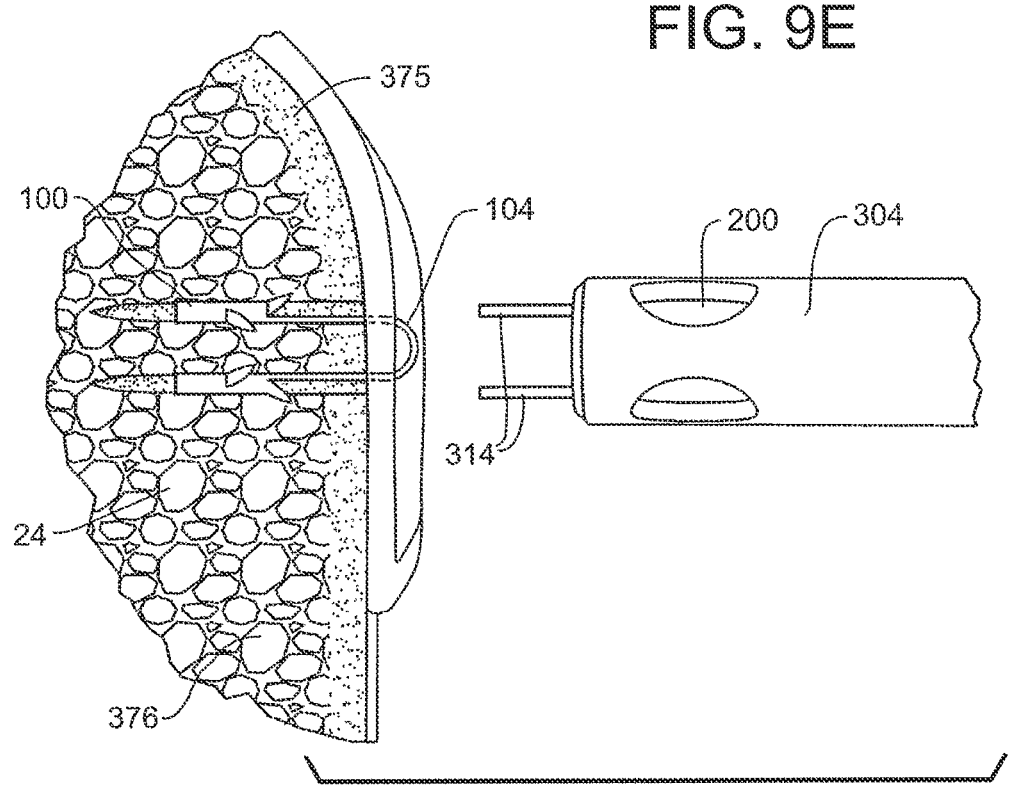
FIG. 9F illustrates a fastener or staple as inserted in accordance with a method of the disclosure; and, FIGS. 10A-10D schematically illustrate alternative position retention members.

Referring to FIG. 9C, the illustration of FIG. 9B is re-illustrated with the pilot hole forming trocar 300 spikes pounded or otherwise driven into the humeral head 24, penetrating the cortical layer 375 into the cancellous portion 376. As illustrated, position retention members 314 also penetrate the bone with the spikes 308. In FIG. 9D, it is illustrated that the trocar 302 and its distal spikes 308 are now removed leaving formed pilot holes 309 with the position retention sleeve 304 remaining in position with position retention member 314 extending into pilot holes 309. The position retention member 304 lumen provides a guide to the pilot holes 309 for a staple delivery device 200. In FIG. 9E, a staple 100 is shown extending into the pilot holes 309 as mounted on the distal end of a staple delivery device 200 that has been inserted into the lumen of position retention member 304. In this position the staple can be delivered and retained in the bone as previously described in the various embodiments disclosed herein. FIG. 9F depicts a staple 100, including bridge 104, as delivered into bone with bridge 104 holding the implant in position on the bone and arms of the staple retaining position in the bone, such as within the cancellous portion 376.

Figure 10A:
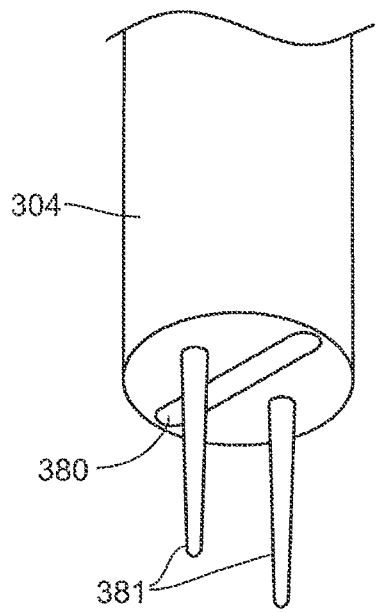
Figure 10B:
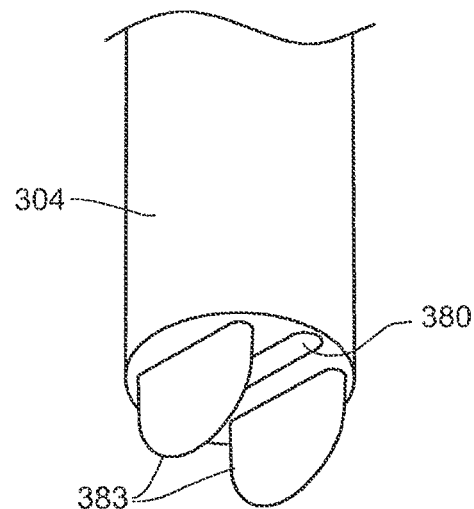
Figure 10C:
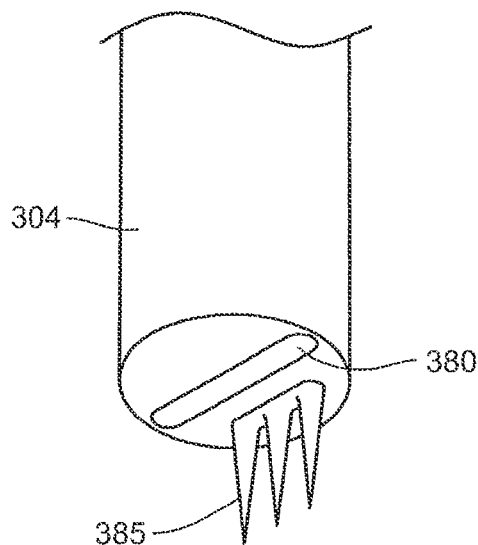
Figure 10D:
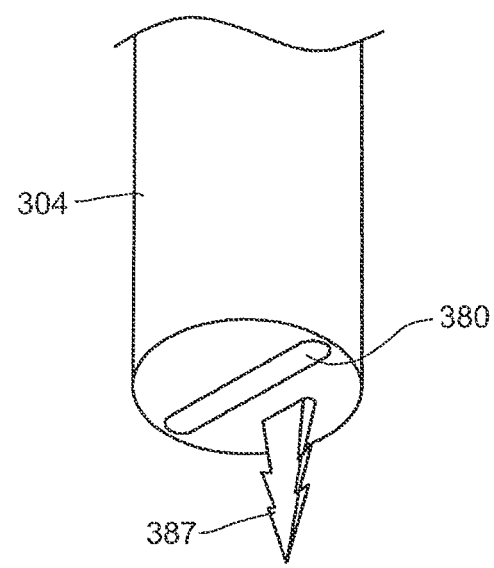

As previously discussed, the position retention members of FIG. 2 can include semi-cylindrical projections that fit within the pilot holes when formed by the spikes. However, alternative embodiments of position retention members are possible with some exemplary elements depicted in FIGS. 10A-10D. Each of these Figures illustrate a distal portion of a position retention sleeve 304. As seen in these exemplary views, the distal end includes a slot or other shaped opening 380 which allows the passage of a distal portion of either a staple delivery device 200 or the spikes 308 of a trocar 302. In FIG. 10A, the position retention members are spikes 381 which are pounded into bone to retain the sleeve's position, but the spikes do not extend into the pilot holes for the staple. FIG. 10B depicts rounded blades 383 that may cut into the bone surface to retain position. Alternatively, FIG. 10C illustrates a series of spikes 385 that may interact with the bone surface to retain position relative to pilot holes when formed. Finally, FIG. 10D illustrates a barbed projection 387 that can be used to retain the position of the instrument with respect to pilot holes formed in bone.

While exemplary embodiments of the present invention have been shown and described, modifications may be made, and it is therefore intended in the appended claims and subsequently filed claims to cover all such changes and modifications which fall within the true spirit and scope of the invention.

What is claimed is:

1. A fastener delivery assembly comprising:
   a staple delivery device including a sheath defining a lumen and having an outer surface; and
   a sleeve defining a lumen and having a distal end and a proximal end,
   wherein the outer surface of the sheath is shaped to cooperate with an interior of the sleeve such that the staple delivery device is rotationally restrained when inserted into the sleeve.

2. The fastener delivery assembly of claim 1, further comprising a pilot hole forming device comprising:
   a shaft extending from a proximal end to a distal end; and
   pilot hole forming members extending distally from the distal end of the shaft and configured to form pilot holes in bone.

3. The fastener delivery assembly of claim 2, wherein an outer surface of the pilot hole forming device is shaped to cooperate with the interior of the sleeve such that the pilot hole forming device is rotationally restrained when inserted into the sleeve.

4. The fastener delivery assembly of claim 2, wherein the pilot hole forming members taper as they extend distally from the distal end of the shaft.

5. The fastener delivery assembly of claim 1, wherein the sleeve comprises position retention members extending from the distal end of the sleeve.

6. The fastener delivery assembly of claim 5, wherein the position retention members are configured to retain a position of the sleeve when the position retention members are inserted into bone.

7. The fastener delivery assembly of claim 5, wherein the position retention members comprise semi-cylindrical projections.

8. The fastener delivery assembly of claim 5, further comprising a pilot hole forming device comprising:
   a shaft extending from a proximal end to a distal end; and
   pilot hole forming members extending distally from the distal end of the shaft.

9. The fastener delivery assembly of claim 8, wherein the position retention members are configured to support the pilot hole forming members as the pilot hole forming members form pilot holes in bone.

10. The fastener delivery assembly of claim 8, wherein the pilot hole forming members are slideable within partial lumens of the position retention members.

11. The fastener delivery assembly of claim 1, wherein the outer surface of the sheath comprises a flat surface that is configured to cooperate with a flat surface of the interior of the sleeve to rotationally restrain the staple delivery device when inserted into the sleeve.

12. The fastener delivery assembly of claim 1, wherein the staple delivery device further comprises:
   a staple delivery rod disposed at least partially within the lumen of the sheath; and
   a handle assembly affixed to a proximal end of the sheath and connected to the staple delivery rod.

13. A fastener delivery tool comprising:
   a sleeve;
   a sheath defining a lumen and having a distal end and a proximal end;
   a staple delivery shaft disposed at least partially within the lumen of the sheath; and
   a handle assembly connected to the proximal end of the sheath and to the staple delivery shaft;
   wherein an outer surface of the sheath is shaped to cooperate with an interior of the sleeve such that the sheath is rotationally restrained when inserted into the sleeve.

14. The fastener delivery tool of claim 13, wherein the outer surface of the sheath comprises a flat surface that is configured to cooperate with a flat surface of the interior of the sleeve to rotationally restrain the sheath when inserted into the sleeve.

15. The fastener delivery tool of claim 13, wherein the staple delivery shaft comprises a pair of stakes configured to carry a staple.

16. The fastener delivery tool of claim 13, wherein the handle assembly operatively slides the staple delivery shaft relative to the sheath.

17. A fastener delivery assembly comprising:
   a sleeve defining a lumen and extending from a proximal end to a distal end; and
   a staple delivery device including a sheath defining an outer surface configured to be inserted into the sleeve such that the staple delivery device is rotationally restrained when received within the sleeve; and a pilot hole forming device configured to be inserted into the sleeve such that the pilot hole forming device is rotationally restrained when received within the sleeve.

18. The fastener delivery assembly of claim 17, wherein the sleeve further comprises position retention members extending distally from the distal end of the sleeve.

19. The fastener delivery assembly of claim 17, wherein the staple delivery device is configured to insert a staple into pilot holes in a bone formed by the pilot hole forming device.

20. The fastener delivery assembly of claim 17 wherein the staple delivery device comprises;

the sheath defining a lumen and having a distal end and a proximal end;

a staple delivery shaft disposed at least partially within the lumen of the sheath; and a handle assembly connected to the proximal end of the sheath and to the staple delivery shaft;

wherein an outer surface of the sheath is shaped to cooperate with an interior of the sleeve such that the staple delivery device is rotationally restrained when inserted into the sleeve.

* * * * *